(12) United States Patent
Ra

(10) Patent No.: US 11,197,960 B2
(45) Date of Patent: Dec. 14, 2021

(54) FILTERING SYRINGE

(71) Applicant: Yong-Kuk Ra, Gumi-si (KR)

(72) Inventor: Yong-Kuk Ra, Gumi-si (KR)

( * ) Notice: Subject to any disclaimer, the term of this patent is extended or adjusted under 35 U.S.C. 154(b) by 642 days.

(21) Appl. No.: 15/768,598

(22) PCT Filed: Oct. 27, 2016

(86) PCT No.: PCT/KR2016/012119
§ 371 (c)(1),
(2) Date: Apr. 16, 2018

(87) PCT Pub. No.: WO2017/074040
PCT Pub. Date: May 4, 2017

(65) Prior Publication Data
US 2018/0304022 A1 Oct. 25, 2018

(30) Foreign Application Priority Data
Oct. 30, 2015 (KR) ........................ 10-2015-0152688

(51) Int. Cl.
*A61M 5/31* (2006.01)
*A61M 5/34* (2006.01)
*A61M 5/32* (2006.01)

(52) U.S. Cl.
CPC ............ *A61M 5/3145* (2013.01); *A61M 5/31* (2013.01); *A61M 5/32* (2013.01); *A61M 5/3202* (2013.01);
(Continued)

(58) Field of Classification Search
CPC ............ A61M 2005/3128; A61M 5/31; A61M 5/3145; A61M 5/32; A61M 5/3202; A61M 5/3293; A61M 5/34
See application file for complete search history.

(56) References Cited

U.S. PATENT DOCUMENTS 4,180,071 A 12/1979 Oiwa
5,222,502 A * 6/1993 Kurose .............. A61B 5/15003
600/576
(Continued)

FOREIGN PATENT DOCUMENTS

KR 10-2012-0087587 8/2012
KR 10-2013-0139807 12/2013
(Continued)

OTHER PUBLICATIONS

English translation of the Written Opinion of International Application No. PCT/KR2016/012119; dated May 1, 2018.
(Continued)

*Primary Examiner* — Brandy S Lee
(74) *Attorney, Agent, or Firm* — LRK Patent Law Firm

(57) ABSTRACT

The present invention relates to a filtering syringe, and more particularly, to an apparatus obtained by improving a syringe provided with a filter means for filtering foreign substances such as glass fragments of an ampoule, so as to prevent the foreign substances from being injected together with a liquid medicine while allowing the liquid medicine to be smoothly sucked and injected with a small force, especially even though a filter means having micro-pores is employed. The filtering syringe is configured such that the filter means is provided in the injection flow passage to prevent the foreign substances from being injected together with the liquid medicine while enabling the liquid medicine to be more smoothly sucked and injected despite employing the filter means having the micro-pores, thereby maximizing user's convenience and marketability of the syringe.

5 Claims, 14 Drawing Sheets

(52) U.S. Cl.
CPC ............ *A61M 5/3293* (2013.01); *A61M 5/34* (2013.01); *A61M 2005/3128* (2013.01)

(56) References Cited

U.S. PATENT DOCUMENTS

| | | | | |
|---|---|---|---|---|
| 6,796,965 | B2 * | 9/2004 | Dumaresq-Lucas | ........................ A61M 5/3145 604/190 |
| 2014/0213982 | A1 * | 7/2014 | Kim | ...................... A61M 5/165 604/190 |

FOREIGN PATENT DOCUMENTS

| KR | 10-1364496 | 2/2014 |
|---|---|---|
| KR | 10-2015-0018336 | 2/2015 |
| KR | 10-1560149 | 10/2015 |
| KR | 10-1563723 | 10/2015 |

OTHER PUBLICATIONS

International Search Report for International Application No. PCT/KR2016/012119, dated Feb. 3, 2017.

* cited by examiner

FIG. 11
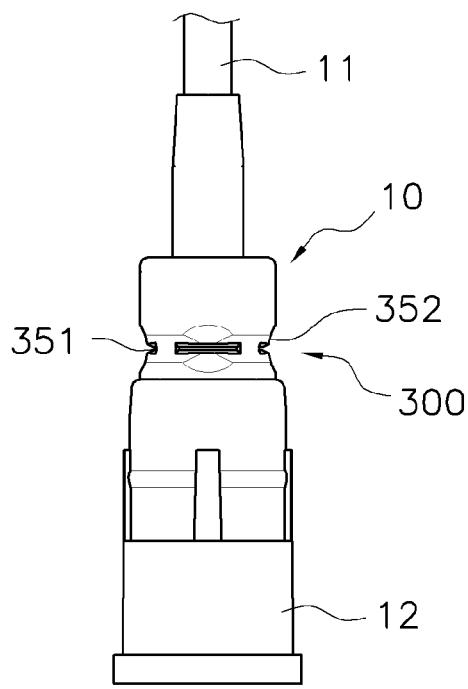
(a)
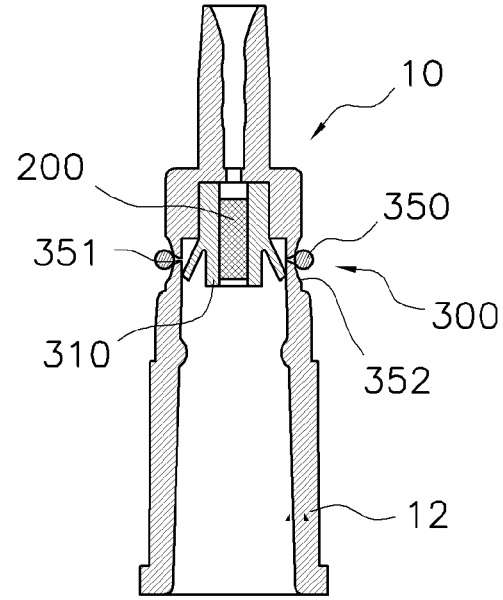
(b)

FILTERING SYRINGE

TECHNICAL FIELD

The present invention relates to a filtering syringe, and more particularly, to an apparatus obtained by improving a syringe provided with a filter means for filtering foreign substances such as glass fragments of an ampoule, so as to prevent the foreign substances from being injected together with a liquid medicine while allowing the liquid medicine to be smoothly sucked and injected with a small force, especially even though a filter means having micro-pores is employed, wherein the apparatus is configured such that the filter means is provided in an injection flow passage to prevent the foreign substances from being injected together with the liquid medicine while enabling the liquid medicine to be more smoothly sucked and injected despite employing the filter means having the micro-pores, thereby maximizing user's convenience and marketability of the syringe.

BACKGROUND ART

In general, a syringe is an instrument for injecting a liquid medicine into a body of an animal/plant and is configured to pierce a skin with a sharp tip thereof to allow the liquid medicine to be injected into any tissue of the body.

FIG. 1 is an exploded perspective view illustrating a conventional syringe. As shown in FIG. 1, the syringe generally includes a cylinder 20 to which an injection needle 10 is coupled and in which an injection liquid is contained, and a plunger 30 provided in the cylinder 20 so as to be movable forward and backward.

In this conventional syringe, as the plunger 30 is retreated, a negative pressure is generated in the cylinder 20 and the cylinder is then filled with an injection liquid. As the plunger is moved forward, the injection liquid in the cylinder 20 is discharged through the injection needle by a positive pressure and then injected into a patient's body.

However, when this conventional syringe is used, there is concern that foreign substances incorporated in the injection liquid itself or foreign substances such as glass particles scattered into and mixed with the injection liquid during a process of breaking and opening an ampoule in which the injection liquid is stored may be injected together with the injection liquid into the patient's body.

To solve this problem, a filtering syringe provided with a filter for filtering foreign substances contained in an injection liquid has been developed.

First, as disclosed in Korean Patent Laid-Open Publication No. 2012-87587, a conventional filtering syringe in which a filter for filtering foreign substances is provided in an injection needle or a cylinder performs a function of filtering foreign substances from an injection liquid sucked into the cylinder.

However, since foreign substances had been stuck to an outer surface of the injection needle introduced into an ampoule when the injection liquid is sucked, or foreign substances incorporated in the injection liquid remaining within the injection needle had not been filtered, it was impossible to fundamentally prevent the foreign substances from being injected together with the injection liquid into a patient's body.

In response thereto, U.S. Pat. No. 4,180,071 discloses an example in which a filter for filtering foreign substances is provided in a cap for covering an injection needle.

FIG. 2 is an exploded perspective view illustrating a conventional filter-cap syringe, and FIG. 3 is a sectional view illustrating a main portion of the conventional filter-cap syringe, wherein FIGS. 2 and 3 illustrate the conventional filter-cap syringe disclosed in U.S. Pat. No. 4,180,071.

Since the conventional filter-cap syringe has a cap 40 with an internal filter 41 provided therein as shown in FIG. 3 so that foreign substances are filtered by the filter 41 when an injection liquid is sucked, and the cap 40 including the filter 41 is detached from an injection needle 10 upon injection of the injection liquid, there is no concern that foreign substances may be injected.

However, the conventional filter-cap syringe has a technical problem in that since the injection liquid may be sucked into a cylinder 20 only via the minute injection needle 10 after passing through the filter 41 provided in the cap 40, a relatively large force is required for sucking the injection liquid and thus it is very inconvenient to use the syringe.

In addition, there is a problematic situation in which as a filter having micro-pores has been recently employed, the liquid medicine may not pass through the filter having the micro-pores and thus may not be smoothly sucked even though the plunger 30 is retreated such that a negative pressure is applied to an interior of the cylinder 20 and the cylinder 20 is then in a vacuum state.

PRIOR ART DOCUMENT

Korean Patent Laid-Open Publication No. 2012-87587.
U.S. Pat. No. 4,180,071.

DISCLOSURE

Technical Problem

The present invention is conceived to solve these problems, and an object of the present invention is to provide a filtering syringe configured such that a filter means is provided in an injection flow passage to prevent foreign substances from being injected together with a liquid medicine while enabling the liquid medicine to be more smoothly sucked and injected despite employing the filter means having micro-pores, thereby maximizing user's convenience and marketability of the syringe.

Technical Solution

According to the present invention, there is provided a filtering syringe including an injection needle, a cylinder and a plunger, wherein the filtering syringe further includes a suction flow passage formed from a pointed hollow cap to the cylinder and provided with a one-way valve means; and an injection flow passage formed from the cylinder to the injection needle and provided with a detachable opening/closing means for selectively opening and closing the injection needle and a filter means for filtering out foreign substances from a liquid medicine, wherein the injection flow passage and the suction flow passage share portions of the flow passages or the injection flow passage is formed independently of the suction flow passage, whereby a flow passage portion from the filter means to the injection needle in the injection flow passage is formed independently of the suction flow passage.

An inlet of the suction flow passage and an outlet of the injection flow passage may be coaxially arranged with each other, and an outlet of the suction flow passage and an inlet of the injection flow passage may be shared. Otherwise, the inlet of the suction flow passage and the outlet of the injection flow passage may not be coaxially arranged with each other, and the outlet of the suction flow passage and the inlet of the injection flow passage may be shared.

A connector may be further provided between the injection needle and the cylinder.

Alternatively, the inlet of the suction flow passage and the outlet of the injection flow passage may be coaxially arranged with each other, and the outlet of the suction flow passage and the inlet of the injection flow passage may not be shared. Otherwise, the inlet of the suction flow passage and the outlet of the injection flow passage may not be coaxially arranged with each other, and the outlet of the suction flow passage and the inlet of the injection flow passage may not be shared.

In this case, it is preferable that the outlet of the suction flow passage and the inlet of the injection flow passage are fixed to be directed in different directions or are angle-adjustable.

In addition, it is most preferable that an adhesive material for securing a needle body and a hub of the injection needle to each other is accommodated in an opening/closing means, which surrounds the injection needle to maintain airtightness, so that the adhesive material is isolated from the liquid medicine.

Advantageous Effects

The filtering syringe of the present invention has advantages in that a filter means is provided in an injection flow passage to prevent foreign substances from being injected together with a liquid medicine while enabling the liquid medicine to be more smoothly sucked and injected despite employing the filter means having micro-pores, thereby maximizing user's convenience and marketability of the syringe.

DESCRIPTION OF DRAWINGS

FIGS. 11 (a) and (b) are views illustrating a still further example of the one-way valve means in the first embodiment of the filtering syringe according to the present invention.

BEST MODE

Figure 1:
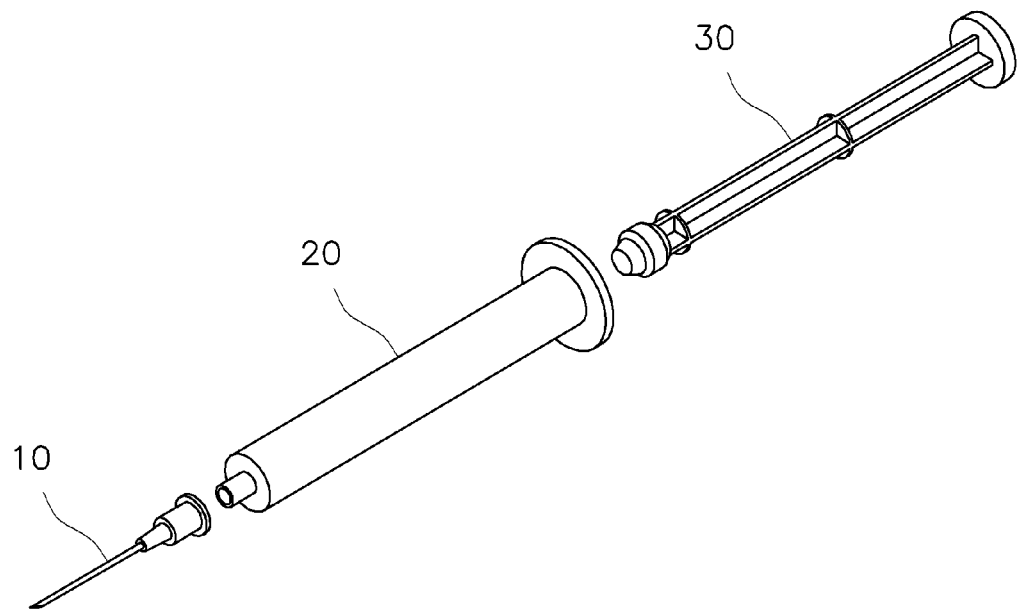
FIG. 1 is an exploded perspective view illustrating a conventional syringe.
Figure 2:
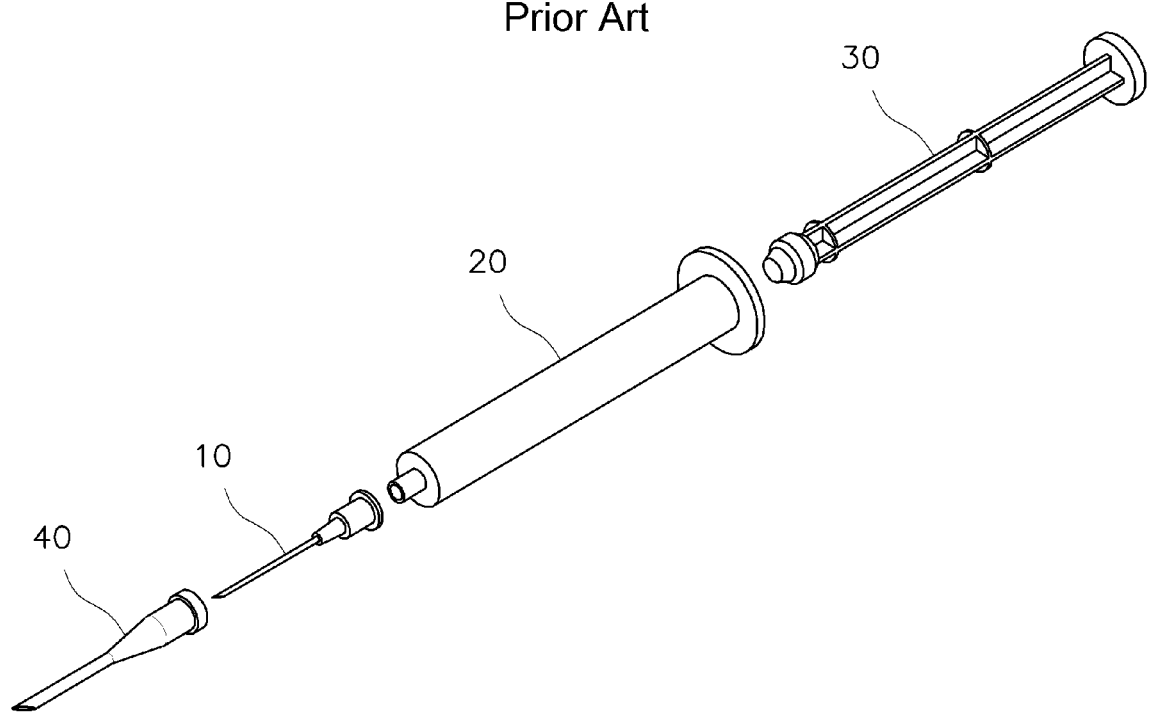
FIG. 2 is an exploded perspective view illustrating a conventional filter-cap syringe.
Figure 3:
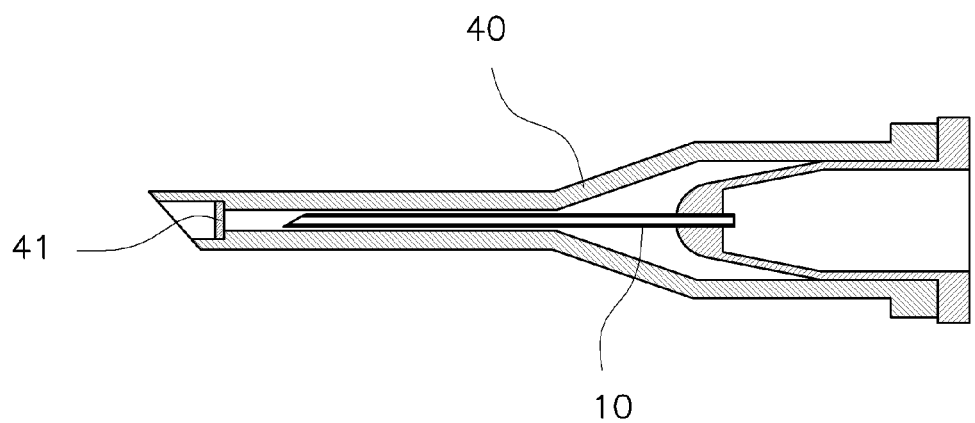
FIG. 3 is a sectional view illustrating a main portion of the conventional filter-cap syringe.
Figure 4:
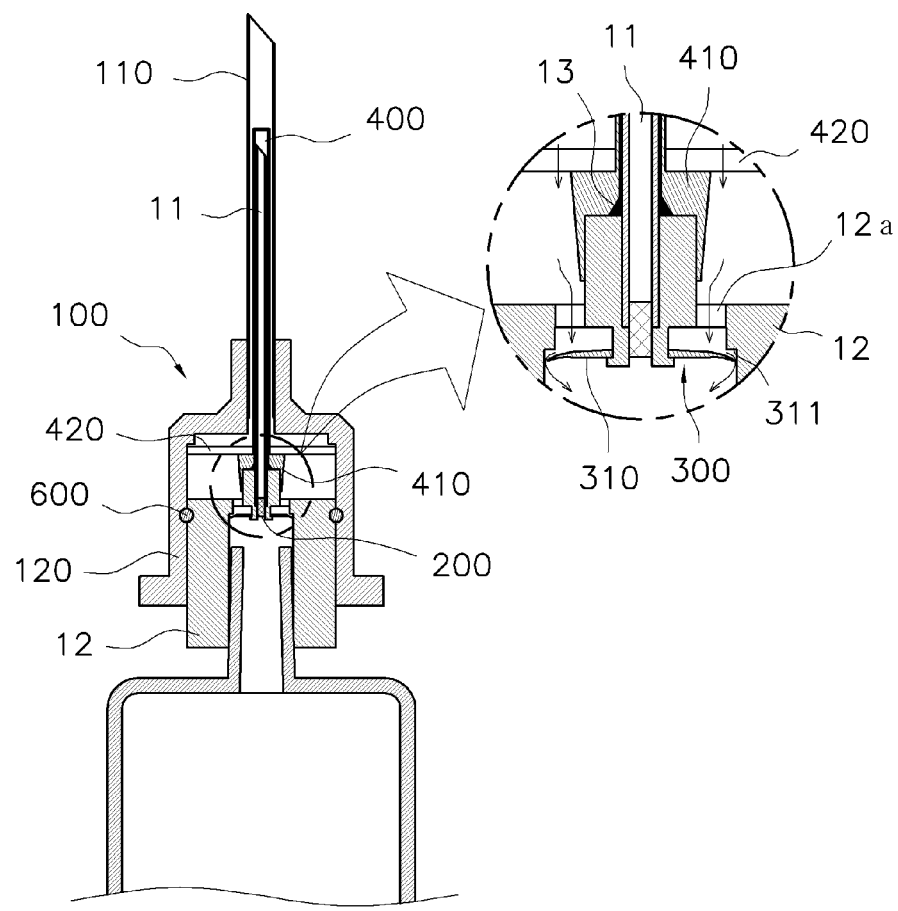
FIG. 4 is a sectional view illustrating a state where a one-way valve means is opened in a first embodiment of a filtering syringe according to the present invention.
Figure 5:
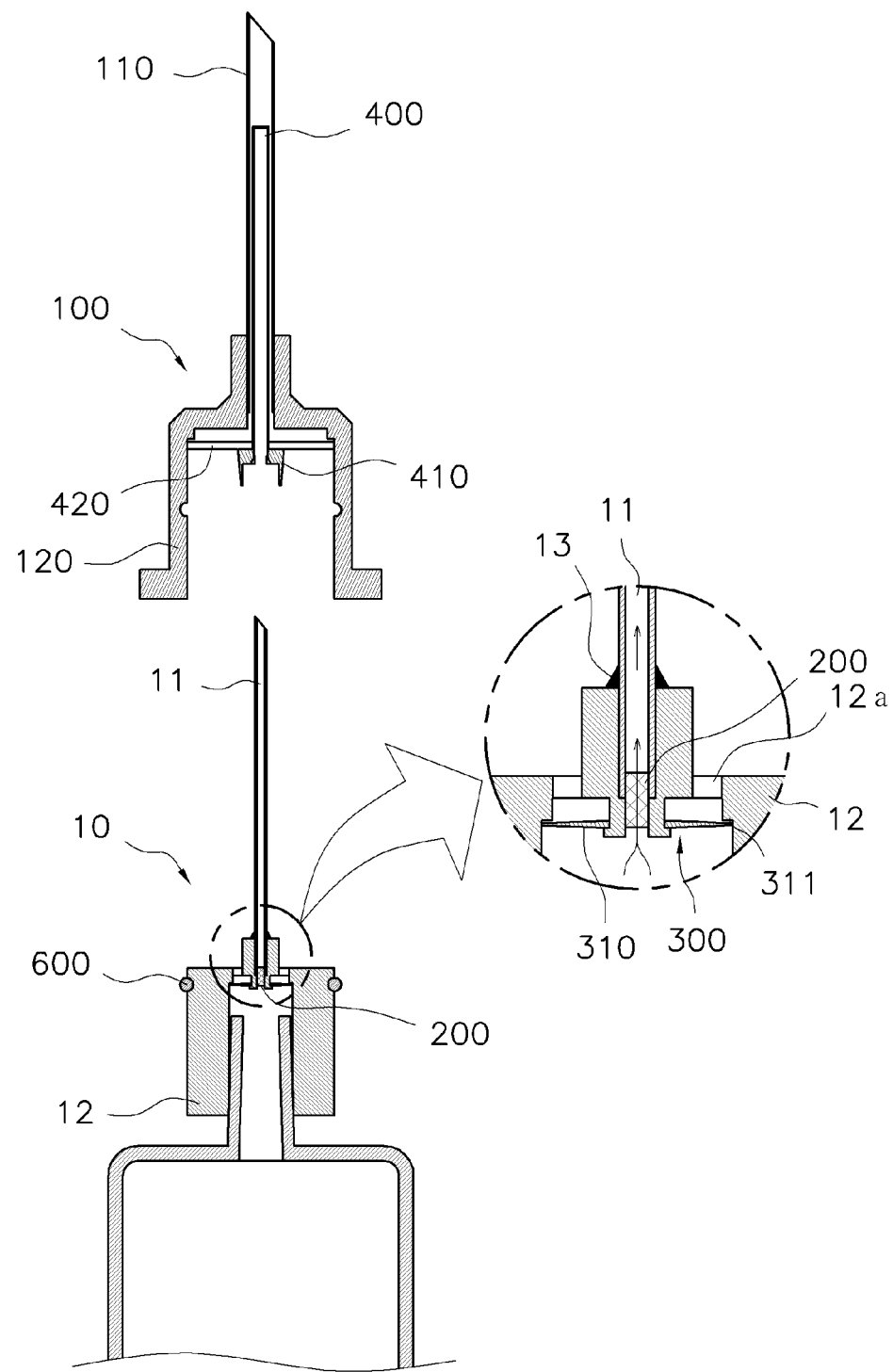
FIG. 5 is a sectional view illustrating a state where the one-way valve means is closed in the first embodiment of the filtering syringe according to the present invention.
Figure 6:
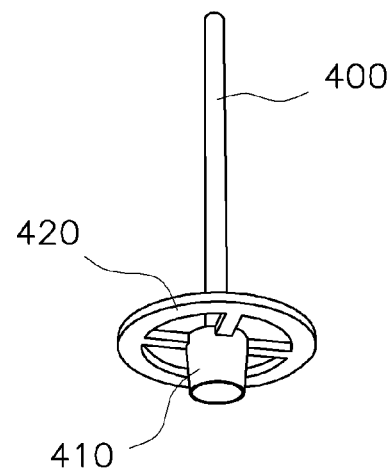
FIG. 6 is a perspective view exemplarily illustrating an opening/closing means in the first embodiment of the filtering syringe according to the present invention.

FIG. 4 is a sectional view illustrating a state where a one-way valve means is opened in a first embodiment of a filtering syringe according to the present invention, FIG. 5 is a sectional view illustrating a state where the one-way valve means is closed in the first embodiment of the filtering syringe according to the present invention, and FIG. 6 is a perspective view exemplarily illustrating an opening/closing means in the first embodiment of the filtering syringe according to the present invention.

Figure 7:
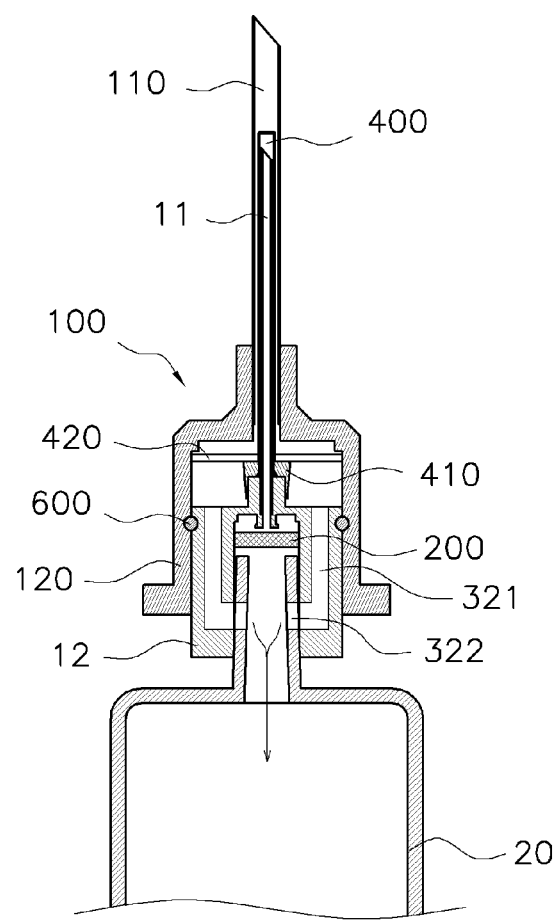
FIG. 7 is a sectional view illustrating a state where another example of the one-way valve means is opened in the first embodiment of the filtering syringe according to the present invention.
Figure 8:
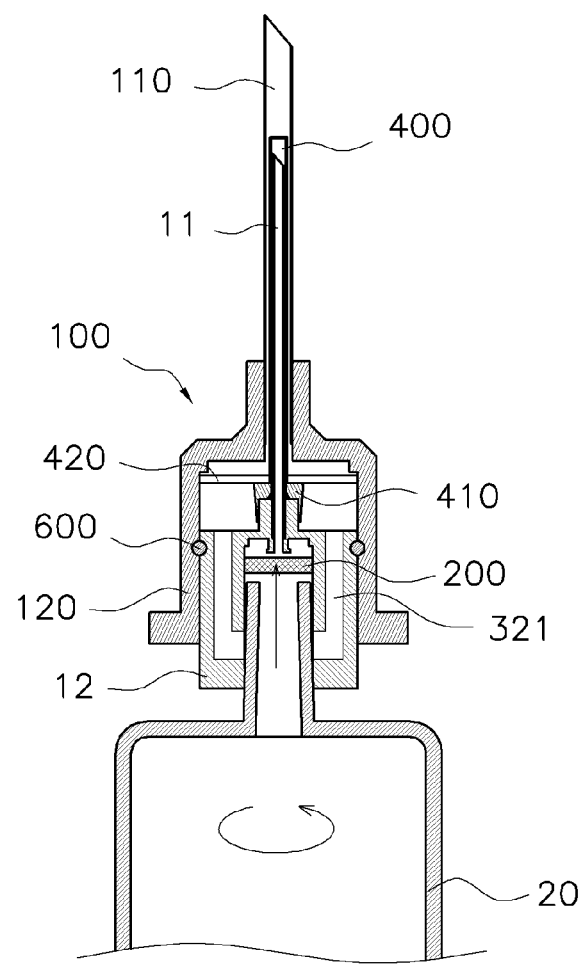
FIG. 8 is a sectional view illustrating a state where the other example of the one-way valve means is closed in the first embodiment of the filtering syringe according to the present invention.

FIG. 7 is a sectional view illustrating a state where another example of the one-way valve means is opened in the first embodiment of the filtering syringe according to the present invention, and FIG. 8 is a sectional view illustrating a state where the other example of the one-way valve means is closed in the first embodiment of the filtering syringe according to the present invention.

Figure 9:
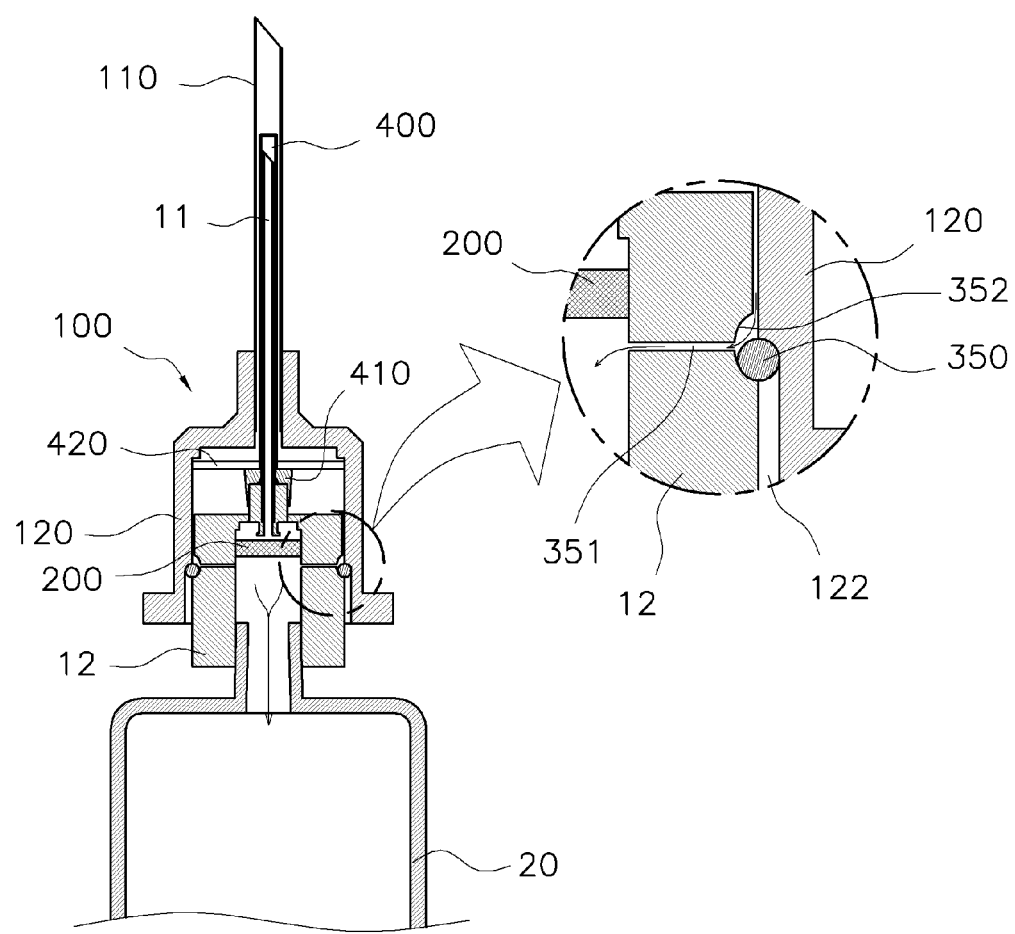
FIG. 9 is a sectional view illustrating a state where a further example of the one-way valve means is opened in the first embodiment of the filtering syringe according to the present invention.
Figure 10:
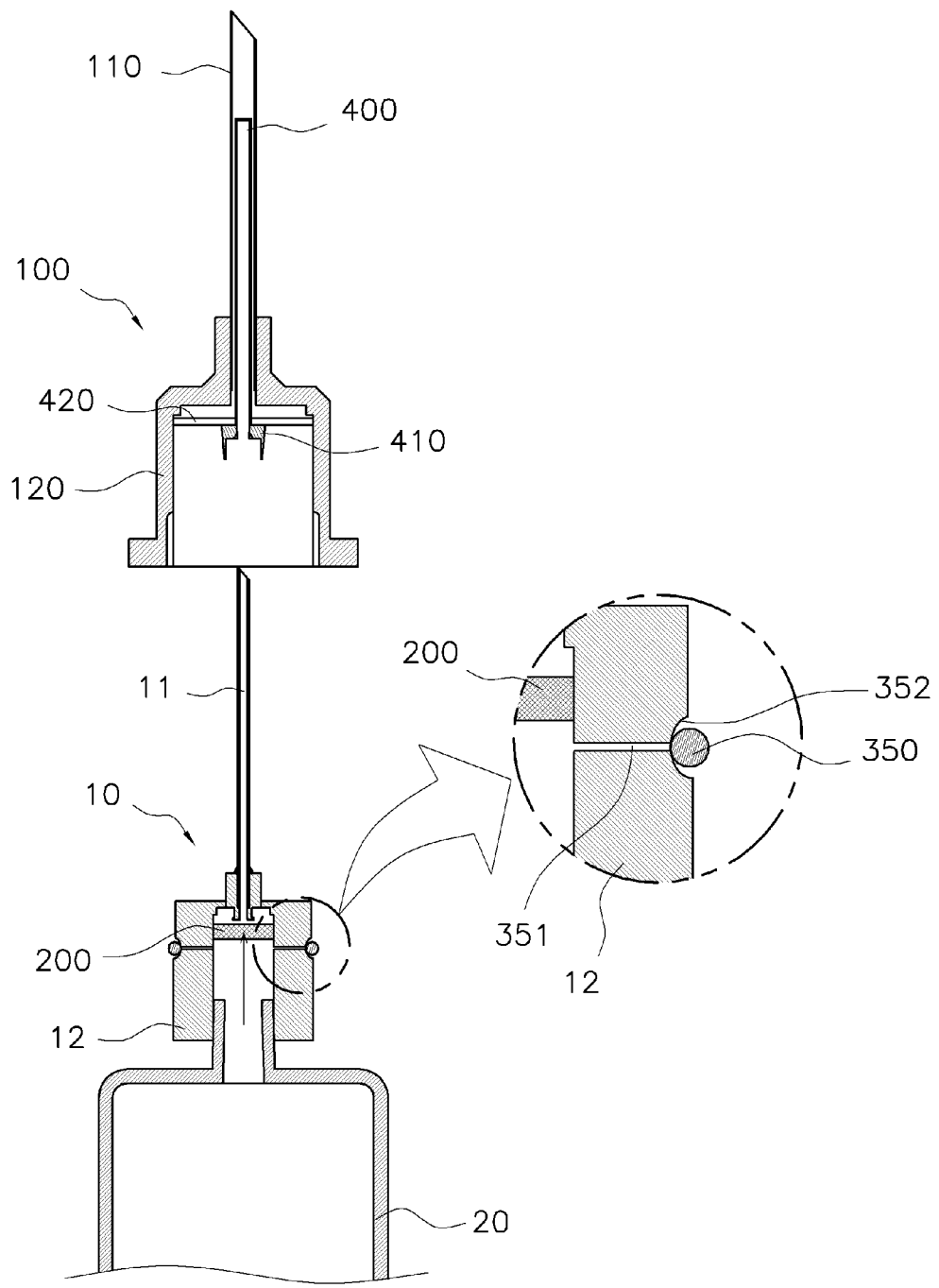
FIG. 10 is a sectional view illustrating a state where the further example of the one-way valve means is closed in the first embodiment of the filtering syringe according to the present invention.

Moreover, FIG. 9 is a sectional view illustrating a state where a further example of the one-way valve means is opened in the first embodiment of the filtering syringe according to the present invention, and FIG. 10 is a sectional view illustrating a state where the further example of the one-way valve means is closed in the first embodiment of the filtering syringe according to the present invention.

Figure 12:
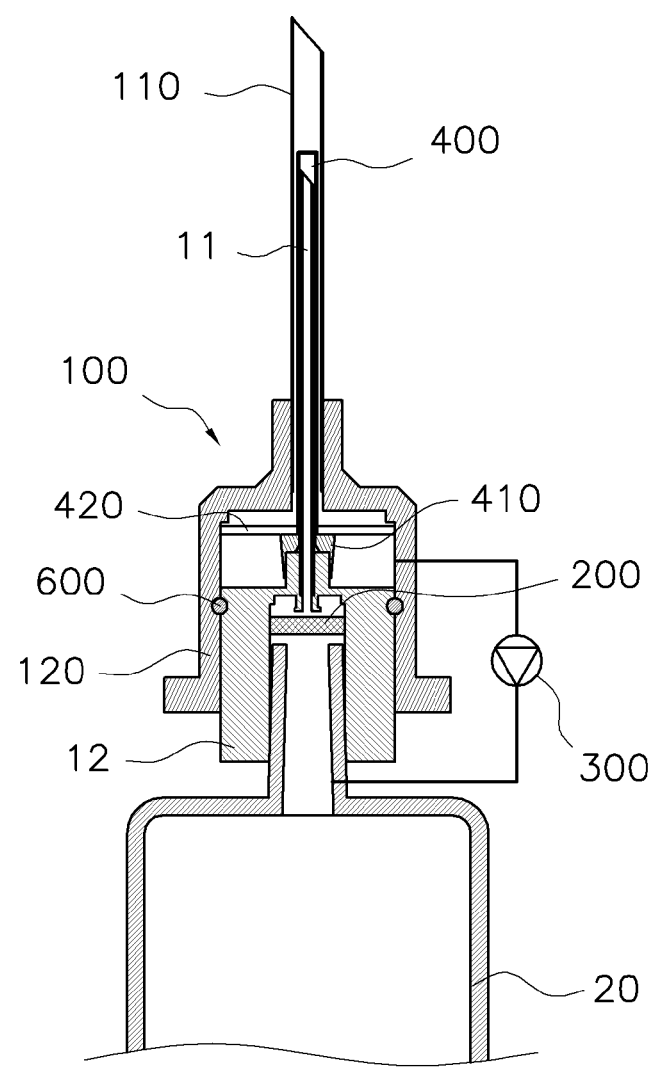
FIG. 12 is a sectional view illustrating a state where the one-way valve means is externally provided in the first embodiment of the filtering syringe according to the present invention.
Figure 13:
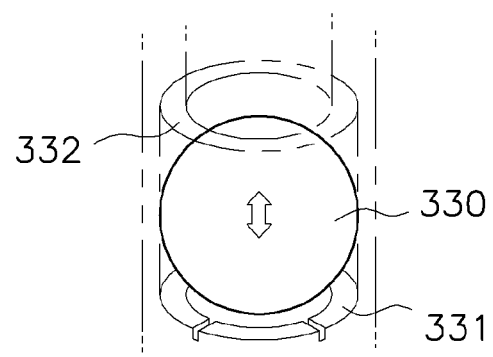
FIG. 13 is a view illustrating one example of the one-way valve means in the first embodiment of the filtering syringe according to the present invention.
Figure 14:
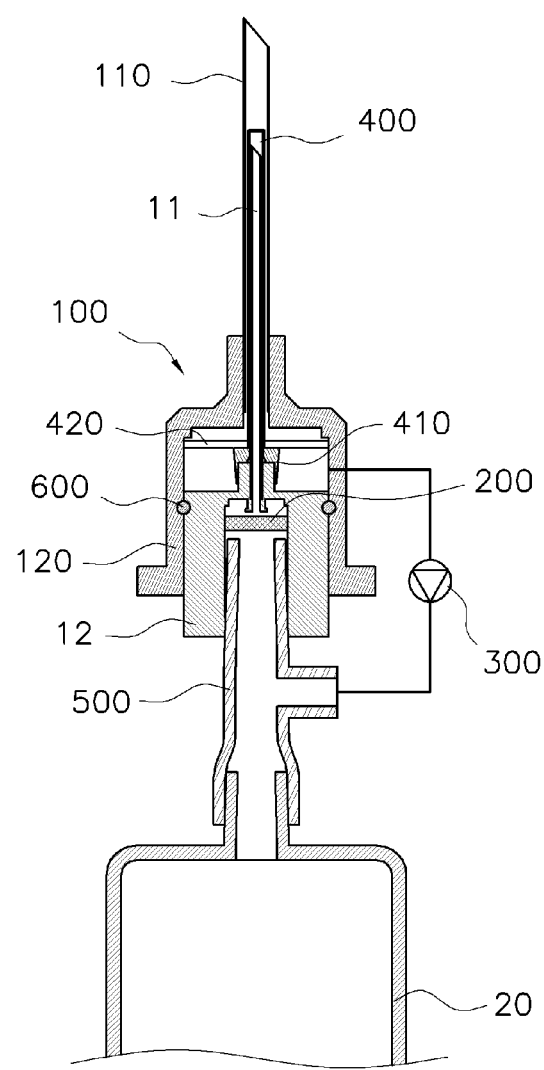
FIG. 14 is a sectional view illustrating a state where the one-way valve means is externally provided and a connector is employed in the first embodiment of the filtering syringe according to the present invention outside.

Furthermore, FIG. 11 is views illustrating a still further example of the one-way valve means in the first embodiment of the filtering syringe according to the present invention, wherein FIG. 11 (a) is a front view and FIG. 11 (b) is a front sectional view. FIG. 12 is a sectional view illustrating a state where the one-way valve means is externally provided in the first embodiment of the filtering syringe according to the present invention, FIG. 13 is a view illustrating one example of the one-way valve means in the first embodiment of the filtering syringe according to the present invention, and FIG. 14 is a sectional view illustrating a state where the one-way valve means is externally provided and a connector is employed in the first embodiment of the filtering syringe according to the present invention outside.

Figure 15:
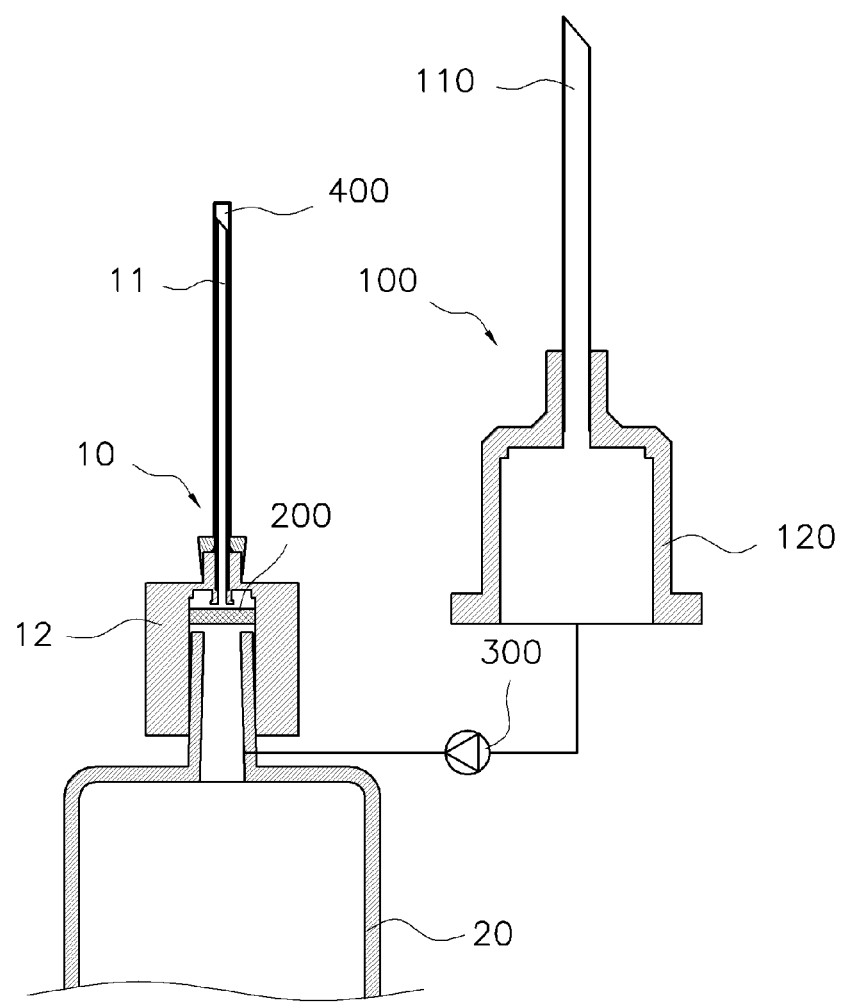
FIG. 15 is a sectional view illustrating a state where a one-way valve means is externally provided in a second embodiment of the filtering syringe according to the present invention.
Figure 16:
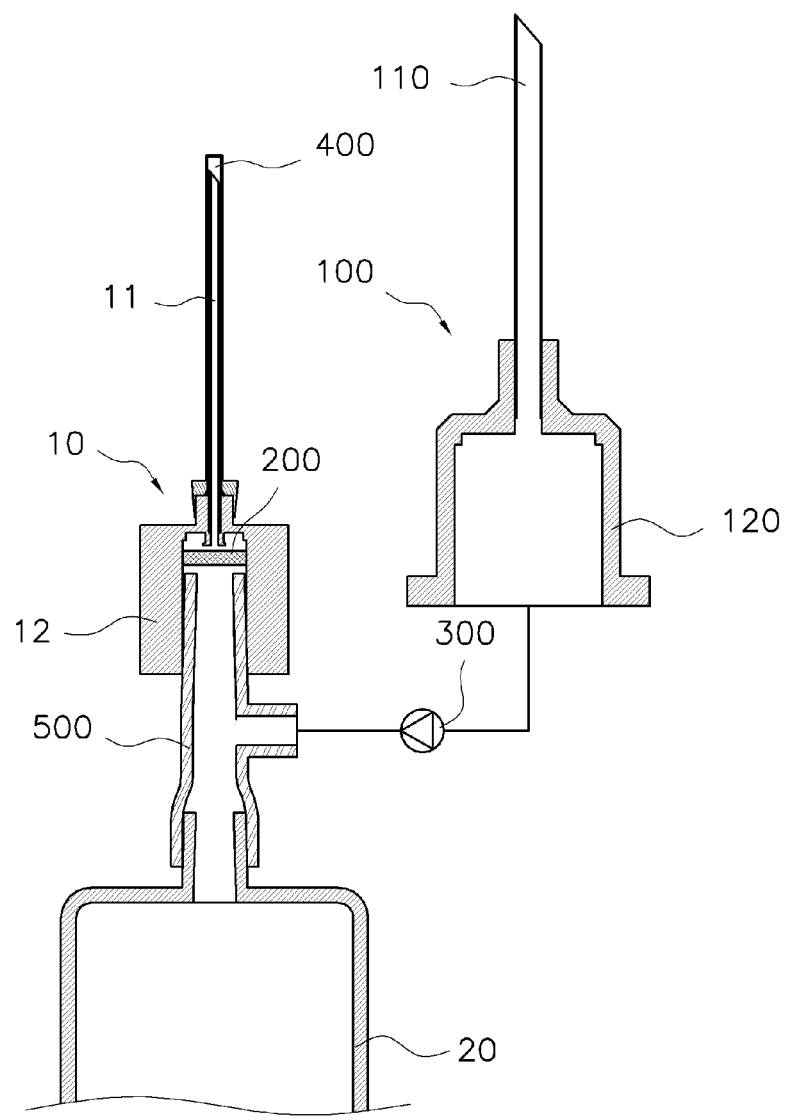
FIG. 16 is a sectional view illustrating a state where the one-way valve means is externally provided and a connector is employed in the second embodiment of the filtering syringe according to the present invention.

In addition, FIG. 15 is a sectional view illustrating a state where a one-way valve means is externally provided in a second embodiment of the filtering syringe according to the present invention, and FIG. 16 is a sectional view illustrating a state where the one-way valve means is externally provided and a connector is employed in the second embodiment of the filtering syringe according to the present invention.

Figure 17:
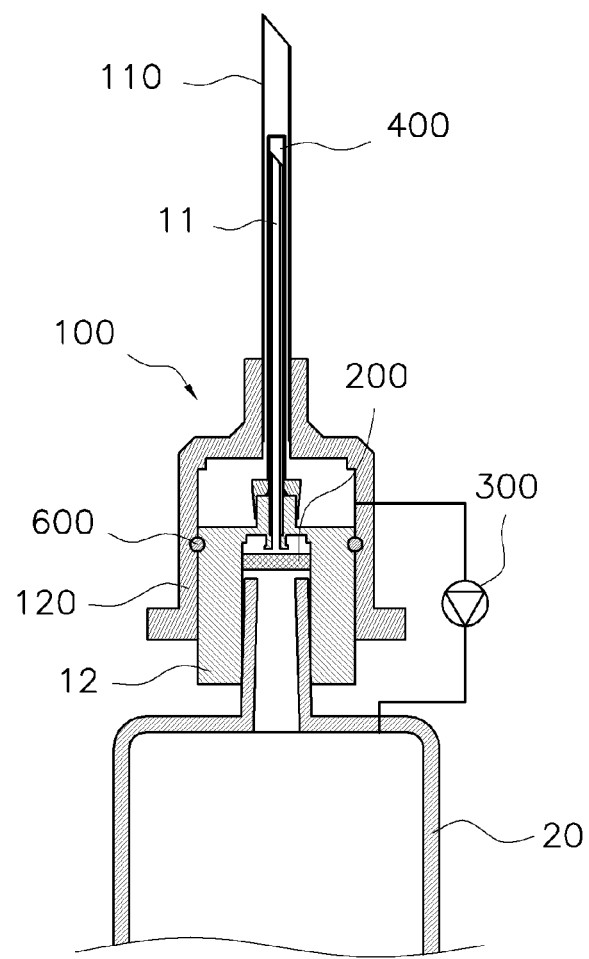
FIG. 17 is a sectional view illustrating a state where a one-way valve means is externally provided in a third embodiment of the filtering syringe according to the present invention.
Figure 18:
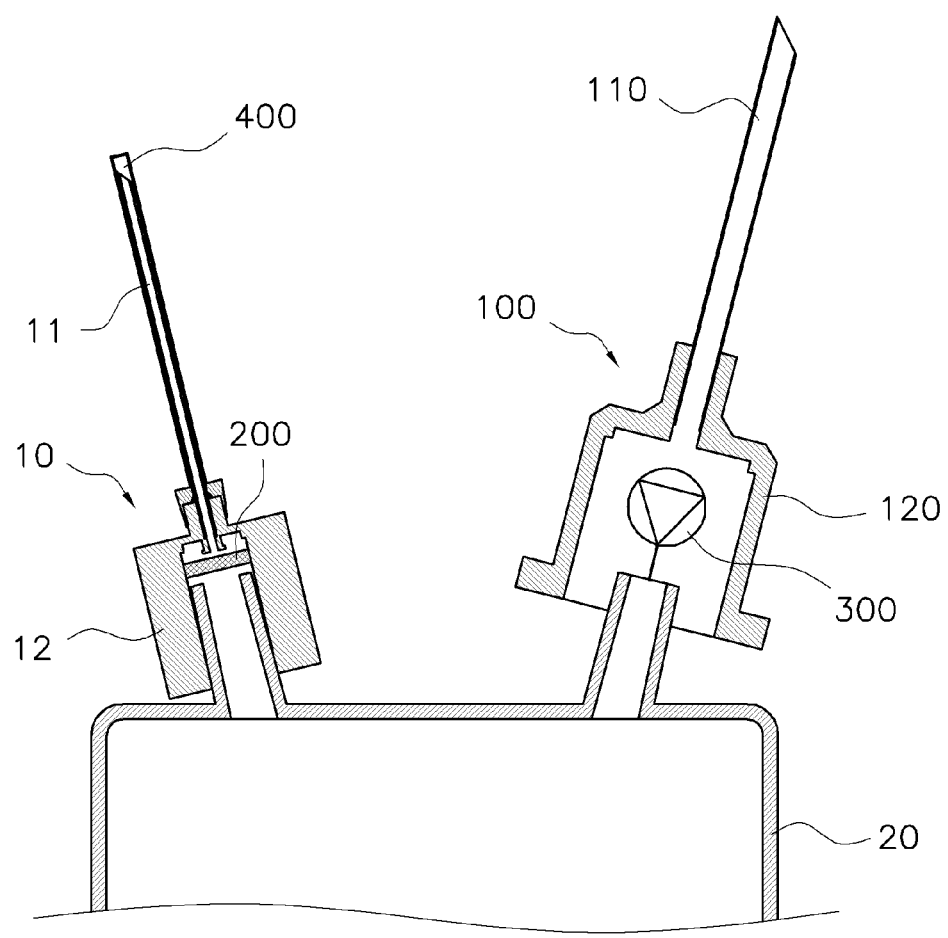
FIG. 18 is a sectional view illustrating a state where a one-way valve means is internally provided in a fourth embodiment of the filtering syringe according to the present invention.

Moreover, FIG. 17 is a sectional view illustrating a state where a one-way valve means is externally provided in a third embodiment of the filtering syringe according to the present invention, and FIG. 18 is a sectional view illustrating a state where a one-way valve means is internally provided in a fourth embodiment of the filtering syringe according to the present invention.

Embodiments of the present invention will be described below in detail with reference to the accompanying drawings.

As shown in FIGS. 4 to 18, the filtering syringe of the present invention is technically characterized in that a suction flow passage for sucking a liquid medicine and an injection flow passage for injecting the liquid medicine are formed inside and outside a well-known syringe such that a flow passage portion from a filter means 200 to an injection needle 10 is formed independently of the suction flow passage, thereby basically preventing the liquid medicine containing foreign substances from being injected and enabling the liquid medicine to be easily sucked with a force less than that required for a conventional syringe.

The filtering syringe includes the injection needle 10, a cylinder 20 and a plunger 30 and further includes the suction flow passage formed from a pointed hollow cap 100 to the cylinder 20 and provided with a one-way valve means 300; and the injection flow passage formed from the cylinder 20 to the injection needle 10 and provided with a detachable opening/closing means 400 for selectively opening and closing the injection needle 10 and the filter means 200 for filtering out foreign substances from the liquid medicine, wherein the injection flow passage and the suction flow passage share portions of the flow passages or the injection flow passage is formed independently of the suction flow passage, whereby the flow passage portion from the filter means 200 to the injection needle 10 in the injection flow passage is formed independently of the suction flow passage.

As such, the suction flow passage and the flow passage from the cylinder 20 to the filter means 200 in the injection flow passage are a section in which a portion of the liquid medicine containing foreign substances such as glass fragments produced upon opening of the liquid medicine-container such as a glass ampoule may remain. By causing this section in which the foreign substances may remain to be formed independently of a flow passage portion from the filter means 200 to the injection needle 10 in the injection flow passage, it is possible to fundamentally prevent foreign substances such as glass fragments from being injected into the body.

In other words, the present invention is to filter the liquid medicine, which may contain any foreign substances, upon injection of the liquid medicine rather than upon suction of the liquid medicine.

This is to improve non-smooth suction of the liquid medicine resulting from employing the fine filter means 200 having micro-pores of about 1.2 μm or less in size, wherein the improvement is focused on operations in which if a same pressure is applied as a negative pressure to suck the liquid medicine, the suction of the liquid medicine may be restricted by the fine filter means 200 having the micro-pores, whereas if the same pressure is applied as a positive pressure to inject the liquid medicine, the injection may be more smoothly made even with the fine filter means 200 having the micro-pores.

To this end, an inlet of the suction flow passage and an outlet of the injection flow passage are formed independently of each other in the present invention. Upon suction of the liquid medicine, the one-way valve means 300 in the suction flow passage is opened, so that the liquid medicine is easily sucked into the cylinder 20 of the syringe regardless diameter of the injection needle 10, while the injection flow passage is closed by the opening/closing means 400 during the suction.

On the contrary, upon injection of the liquid medicine, the suction flow passage is closed by the one-way valve means 300, while the injection flow passage is opened by removing the opening/closing means 400, so that the filter means 200 filters out foreign substances from the liquid medicine that in turn is injected.

According to the embodiments, opening or closing of the one-way valve means 300 may be automatically adjusted depending on a direction of pressure on the liquid medicine, may be adjusted in response to a user's rotation manipulation, or may be adjusted depending on simply whether a cap 100 is separated. Alternatively, the one-way valve means 300 may be a pointed penetration needle for penetrating a soft sealing material.

In implementing the filtering syringe of the present invention as described above, there may be the following four examples depending on combinations of whether the inlet of the suction flow passage and the outlet of the injection flow passage are coaxially arranged with each other and whether an outlet of the suction flow passage and an inlet of the injection flow passage are shared on the cylinder 20 of the syringe. These examples will be described below by classifying them into first to fourth embodiments.

First embodiment: Example in which the inlet of the suction flow passage and the outlet of the injection flow passage are coaxially arranged with each other, and the outlet of the suction flow passage and the inlet of the injection flow passage are shared.

Second embodiment: Example in which the inlet of the suction flow passage and the outlet of the injection flow passage are not coaxially arranged with each other, and the outlet of the suction flow passage and the inlet of the injection flow passage are shared.

Third embodiment: Example in which the inlet of the suction flow passage and the outlet of the injection flow passage are coaxially arranged with each other, and the outlet of the suction flow passage and the inlet of the injection flow passage are not shared.

Fourth embodiment: Example in which the inlet of the suction flow passage and the outlet of the injection flow passage are not coaxially arranged with each other, and the outlet of the suction flow passage and the inlet of the injection flow passage are not shared.

(1) First Embodiment

Example in which the inlet of the suction flow passage and the outlet of the injection flow passage are coaxially arranged with each other, and the outlet of the suction flow passage and the inlet of the injection flow passage are shared.

The first embodiment of the filtering syringe according to the present invention may be classified into an example in which the one-way valve means 300 is embedded in the filtering syringe and an example in which the one-way valve means 300 is externally provided.

First, the example of the first embodiment of the filtering syringe according to the present invention in which the one-way valve means 300 is embedded in the filtering syringe is illustrated in FIGS. 4 to 14.

In particular, FIGS. 4 and 5 show the filtering syringe employing the one-way valve means 300, which is automatically opened and closed depending on a direction of pressure on the liquid medicine, wherein the suction flow passage consists of a suction needle 110 of the cap 100→a cap hub 120 of the cap 100→the one-way valve means 300→a hub 12 of the injection needle 10→the cylinder 20.

The cap 100 is to suck the liquid medicine from the liquid medicine-container, and includes the suction needle 110 and the cap hub 120. A tip of the suction needle 110 is inclined and pointed to penetrate a vial or the like and is made of a metal material or a synthetic resin material so that it has a high strength.

In addition, the cap hub 120 is integrally coupled to and supports the suction needle 110, wherein an inner peripheral surface of the cap hub 120 is coupled to an outer peripheral surface of the hub 12 that supports a needle body 11 of the injection needle 10, thereby maintaining airtightness below through-holes 12a formed in the hub.

Here, the needle body 11 and the hub 12 of the injection needle 10 are fixed to each other by an adhesive material 13 such as epoxy, wherein the hub 12 is hermetically assembled to the cylinder 20 of the syringe.

A sealing means 600 such as a separate elastic seal may be additionally provided between the inner peripheral surface of the cap hub 120 and the outer peripheral surface of the hub 12 to prevent the liquid medicine from leaking through a gap therebetween.

In addition thereto, the hub 12 of the injection needle 10 is provided with the filter means 200 having a known configuration for filtering foreign substances such as fine glass fragments, and the one-way valve means 300 that is automatically opened or closed depending on the direction of pressure on the liquid medicine is embedded in the hub 12 of the injection needle 10 such that the one-way valve means 300 is below the filter means 200 and in communication with the through-holes 12a.

This one-way valve means 300 may include a circular elastic plate 310, which is made of, for example, a flexible material such as silicone, and a stepped portion 311.

The elastic plate 310 is formed to have a diameter corresponding to an inner diameter of the hub 12 so that a center portion of the elastic plate is assembled and fixed below the filter means 200 in the hub 12, and the stepped portion 311 is formed above an outer peripheral edge of the elastic plate 310 so as to limit upward deformation of the elastic plate 310.

As a result, upon suction of the liquid medicine, the one-way valve means 300 is opened while the outer peripheral edge of the elastic plate 310 is deformed downward as shown in FIG. 4, so that the liquid medicine passes through the suction flow passage without passing through the filter means 200 and fills the cylinder 20 of the syringe.

Moreover, as shown in FIG. 5, the injection flow passage consists of the cylinder 20→the hub 12 of the injection needle 10→the filter means 200→the needle body 11 of the injection needle 10.

Since the outer peripheral edge of the elastic plate 310 in the one-way valve means 300 is contacted with the stepped portion 311 to limit upward deformation of the elastic plate 310 as shown in FIG. 5, the one-way valve means 300 is closed to prevent the liquid medicine from leaking to the suction flow passage.

In addition thereto, although the needle body 11 of the injection needle 10 is closed by the opening/closing means 400 upon suction of the liquid medicine, the opening/closing means 400 is separated to open the needle body 11 upon injection of the liquid medicine.

In particular, in the present invention, the opening/closing means 400 may be configured to include a hermetic space 410 and a flange 420 as shown in FIG. 6.

In other words, the opening/closing means 400 has functions of closing the needle body 11 of the injection needle 10 upon suction of the liquid medicine and of opening the needle body 11 of the injection needle 10 upon injection of the liquid medicine. In the present invention, it is preferable that the opening/closing means 400 can be coupled to the hub 12 of the injection needle 10.

To this end, the hermetic space 410 is formed at a lower portion of the opening/closing means 400 so that the hermetic space 410 may surround and be coupled to the hub 12 of the injection needle 10.

In particular, in the present invention, it is preferable that an adhesive material 13 for securing the needle body 11 and the hub 12 of the injection needle 10 to each other is accommodated in the hermetic space 410 of the opening/closing means 400, which surrounds the injection needle 10 to maintain airtightness, so that the adhesive material is isolated from the liquid medicine.

With this configuration, it is possible to prevent degradation of an adhesive force of the adhesive material 13 due to contact of the adhesive material 13 with the liquid medicine, or alteration of components of the liquid medicine caused by the adhesive material 13.

In addition thereto, the flange 420 provided in the opening/closing means 400 enables the opening/closing means 400 to be secured to the inner peripheral surface of the cap hub 120, if necessary.

FIG. 5 illustrates that the opening/closing means 400 is fixedly installed within the cap 100 so that the opening/closing means 400 is separated together with the cap 100 in response to separation of the cap 100, thereby opening the injection needle 10.

Accordingly, upon suction of the liquid medicine, the liquid medicine is sucked from the cap 100 into the cylinder through the one-way valve means 300, and upon injection of the liquid medicine, the liquid medicine is injected from the cylinder 20 through the injection needle 10 via the filter means 200.

As a result, for the flow passage portion from the filter means 200 to the injection needle 10 in the injection flow passage, the filter means 200 performs filtering of the liquid medicine in which the foreign substances such as glass fragments may remain, so that the foreign substances are fundamentally prevented from being injected. In particular, since the filter means 200 is provided in the injection flow passage, the liquid medicine can be more smoothly sucked and the injection of the liquid medicine can be easily performed even with the filter means 200 having the micro-pores.

In other words, if the filter means 200 having the micro-pores is employed in the suction flow passage, the liquid medicine cannot easily pass through the filter means 200 even though vacuum is produced within the cylinder 20 upon suction of the liquid medicine, resulting in non-smooth suction of the liquid medicine. However, according to the present invention, this problem can be solved, and upon subsequent injection of the liquid medicine, the liquid medicine can surely pass through the filter means 200 having the micro-pores and can be then be injected since a positive pressure is applied to the liquid medicine.

Although the foregoing has illustrated that the filter means 200 is provided within the hub 12 and the one-way valve means 300 is disposed below the filter means 200 in the hub 12, the filter means 200 may be provided within the hub 12 and the one-way valve means 300 may be disposed within the cylinder 20 of the syringe, for example.

In a modified case, the filter means 200 may be disposed within the cylinder 20 of the syringe and the one-way valve means 300 may be disposed within the cylinder 20 of the syringe but below the filter means 200.

Similarly, a separate connector 500 may be added between the hub 12 and the cylinder 20, the filter means 200 may be provided within the hub 12 and the one-way valve means 300 may be provided within the connector 500. Alternatively, the filter means 200 may be provided within the connector 500 and the one-way valve means 300 may be disposed within the cylinder 20 of the syringe.

In other words, there is no limitation on the positions of the filter means 200 and the one-way valve means 300 in the present invention, and it is merely required that the filter means 200 should be placed closer to the injection needle 10 than the one-way valve means 300 is.

Next, an example in which the opening or closing of the one-way valve means 300 in the first embodiment of the filtering syringe according to the present invention is adjusted in response to a user's rotation manipulation will be described with reference to FIGS. 7 and 8.

Even in this case, the suction flow passage consists of the suction needle 110 of the cap 100→the cap hub 120 of the cap 100→the one-way valve means 300→the hub 12 of the injection needle 10→the cylinder 20.

Furthermore, description of a configuration overlapping with that of the embodiment in which the one-way valve means 300, which is automatically opened or closed depending on the direction of pressure on the liquid medicine as described above, is employed will be omitted. An operation of the one-way valve means 300 which is different from that in the previous embodiment will be described below.

The hub 12 of the injection needle 10 is formed with a passage 321 communicating with the cap hub 120, and the cylinder 20 of the syringe is formed with an opening 322 corresponding to the passage 321.

Accordingly, when the cylinder 20 is rotated and the opening 322 and the passage 321 are selectively aligned with each other, the suction of the liquid medicine is enabled. When the cylinder 20 is further rotated to release such alignment, the opening 322 and the passage 321 are not aligned with each other to block communication therebetween, thereby preventing backflow of the liquid medicine into the suction flow passage upon injection of the liquid medicine.

Next, an example in which the opening or closing of the one-way valve means 300 in the first embodiment of the filtering syringe according to the present invention is controlled depending on simply whether the cap 100 is separated will be described with reference to FIGS. 9 and 10.

Even in this case, the suction flow passage consists of the suction needle 110 of the cap 100→the cap hub 120 of the cap 100→the one-way valve means 300→the hub 12 of the injection needle 10→the cylinder 20.

The hub 12 of the injection needle 10 is provided with flow holes 351 formed to extend from the inner peripheral surface to the outer peripheral surface of the hub as shown in FIGS. 9 and 10, and a groove 352 is formed on the outer peripheral surface of the hub 12 along an entire perimeter of the hub around the flow holes 351.

The diameter and number of the flow holes 351 may be appropriately changed such that the liquid medicine may flow smoothly and airtightness may be achieved, and the groove 352 is formed to have a gently curved surface. An elastic band 350 made of an elastic material such as rubber and having a generally circular cross-section is placed in the groove 352.

This elastic band 350 is elastically disposed in the groove 352 so that the position of the elastic band may be moved depending on whether the elastic band is in contact with the cap hub 120 of the cap 100.

To this end, an engagement ledge 122 for contact with the elastic band 350 is formed on the inner peripheral surface of the cap hub 120.

Accordingly, in a state where the cap 100 is assembled to the injection needle 10, as shown in FIG. 9, the elastic band 350 is brought into contact with the engagement ledge 122 and then moved, so that the flow holes 351 are opened.

On the contrary, in a state where the cap 100 is separated from the injection needle 10, as shown in FIG. 10, the elastic band 350 is contracted to its minimum diameter and then rides on the curved surface and is returned to its original position, so that the flow holes 351 are closed.

As a result, the user can intermittently control the opening or closing of the one-way valve means 300 depending on whether the cap 100 is assembled. When it is intended that the saline solution is sucked and then injected into the liquid medicine-container for accommodating the powdered medicament so that the powdered medicament is dissolved and subsequently the resulting liquid medicine is sucked again, there is an advantage in that suction and injection may be smoothly performed with a smaller force by the aforementioned one-way valve means 300.

Subsequently, when the liquid medicine is intended to be injected into the body and thus the cap 100 is simply separated, the injection flow passage consists of the cylinder 20→the hub 12 of the injection needle 10→the filter means 200→the needle body 11 of the injection needle 10, as shown in FIG. 10.

Even in this case, the opening/closing means 400 is fixedly installed within the cap 100 to allow the opening/closing means 400 to be separated together with the cap 100 in response to the separation of the cap 100, thereby enabling the injection needle 10 to be opened.

Accordingly, upon suction of the liquid medicine, the liquid medicine is sucked from the cap 100 into the cylinder through the one-way valve means 300, whereas upon injection of the liquid medicine, the liquid medicine is injected from the cylinder 20 through the injection needle 10 via the filter means 200.

As a result, it is possible to quickly suck and then rapidly discharge the liquid medicine, as required.

FIG. 11 shows that two one-way valve means 300 are formed in a dual configuration. In this case, a first one-way valve means 300 formed with modified flow holes 351 and groove 352 may be provided on the hub 12 of the injection needle 100, and opening or closing of the first one-way valve means 300 can be controlled depending on whether the cap 100 is assembled. A second one-way valve means 300 comprised of an elastic plate 310 having a modified shape may be provided within the hub 12.

As for the second one-way valve means 300, the elastic plate 310 does not require the separate stepped portion and a generally inclined wing-shaped structure is brought into direct contact with an inner wall of the hub 12 depending on the direction of pressure on the liquid medicine, thereby performing the opening or closing of the second one-way valve means 300.

As such, it is also possible to configure the filtering syringe by including two or more one-way valve means 300.

Next, an example in which the one-way valve means 300 in the first embodiment of the filtering syringe according to the present invention is externally provided will be illustrated in FIGS. 12 to 14.

Although the examples in which the one-way valve means 300 is embedded in the cap 100 or the injection needle 10 have been described above, a force required for sucking the liquid medicine may be utilized when the liquid medicine passes through the one-way valve means 300.

That is, although the one-way valve means 300 is necessarily designed to be large in size so as to perform suction of the liquid medicine with a smaller force, the one-way valve means 300 is embedded in a conventional syringe, whereby there is limitation on enlargement of the filtering syringe in size.

Therefore, in the present invention, it is possible to add an external suction flow passage extending from the cap hub 120 of the cap 100 to the cylinder 20 of the syringe as shown in FIGS. 12 to 14.

In this manner, it is possible to eliminate limitation on the sizes of the one-way valve means 300.

FIG. 12 illustrates an example in which the one-way valve means 300 is separately provided outside.

The one-way valve means 300 may be variously modified to, for example, a check valve having a sphere illustrated in FIG. 13 embedded therein and no limitation on the size thereof, other than the aforementioned examples.

For example, as shown in FIG. 13, the one-way valve means 300 is a known check valve including the sphere 330 for selectively opening and closing the flow passage.

The check valve including the sphere 330 has valve seats 331 and 332 on both sides of the movable sphere 330, wherein one of the valve seat 331 is formed to have a cut-out portion so as to allow a flow of the liquid medicine and the opposite valve seat 332 is configured to contact an outer surface of the sphere 330, thereby maintaining airtightness.

As a result, when a negative pressure is applied in the cylinder 20 of the syringe, the sphere 330 is moved toward the cut-out valve seat 331 so that the liquid medicine can flow through the cut-out portion; whereas when a positive pressure is applied in the cylinder 20 of the syringe, the sphere 330 is moved toward the valve seat 332 to maintain airtightness, thereby blocking the flow of the liquid medicine.

In this case, an additional structure for forming a flow passage between the cap 100 and the cylinder 20 may be added.

For example, a branch tube may be formed integrally with each of the cap hub 120 and the cylinder 20 and the branch tubes of them may be then connected by a tube made of a flexible material to each other. In addition, the branch tubes may be configured to be at certain angles and may also have a well-known configuration enabling selective connection or disconnection of the branch tubes.

In the configuration for disconnecting the tubes from each other, there would no leakage of the liquid medicine only if a state where the one-way valve means 300 is connected to the cylinder 20 should be maintained.

Moreover, FIG. 12 shows that only the one-way valve means 300 is externally provided, and FIG. 14 shows an example in which the one-way valve means 300 is externally provided by using a separate connector 500.

This connector 500 may be formed integrally with the cap hub 120 or the cylinder 20, the one-way valve means 300 may be embedded in the connector 500, and there will be no limitation on modification thereof.

(2) Second Embodiment

Example in which the inlet of the suction flow passage and the outlet of the injection flow passage are not coaxially arranged with each other, and the outlet of the suction flow passage and the inlet of the injection flow passage are shared.

Next, the second embodiment of the present invention is a case in which the outlet of the suction flow passage and the inlet of the injection flow passage are shared, whereas the inlet of the suction flow passage and the outlet of the injection flow passage are not coaxially arranged with each other.

To this end, the cap 100 and the injection needle 10 are independently placed, and the opening/closing means 400 is separated from the cap 100 and is provided to close the injection needle 10.

In this case, as shown in FIG. 15, the one-way valve means 300 is provided on the suction flow passage. The suction flow passage extending from the cap 100 to the cylinder 20 may be flexibly configured, although it will be also possible to configure this suction flow passage to be maintained at a certain angle different from that of the flow passage from the cylinder 20 to the injection needle 10.

Accordingly, the suction flow passage may be formed at one of bodies branched at different angle from the cylinder 20, and the injection flow passage may be formed at the other of the bodies.

With this configuration, the liquid medicine is sucked through the cap 100 in a state where the injection flow passage is closed by the opening/closing means 400, whereby the sucked liquid medicine passes through the one-way valve means 300 and fills the cylinder 20, and the liquid medicine to be injected may be discharged via the filter means 200 to the injection needle 10 from which the opening/closing means 400 has been removed.

FIG. 16 shows a configuration in which the separate connector 500 is added, and illustrates the connector 500 having a perpendicular branch, but the connector may be configured to have a differently angled branch, or it is also preferable to configure the connector to have an angle-adjustable branch. It is also possible to provide the one-way valve means 300 within the connector 500.

(3) Third Embodiment

Example in which the inlet of the suction flow passage and the outlet of the injection flow passage are coaxially arranged with each other, and the outlet of the suction flow passage and the inlet of the injection flow passage are not shared.

FIG. 17 illustrates a case in which the inlet of the suction flow passage and the outlet of the injection flow passage are coaxially arranged with each other as described above, whereas the outlet of the suction flow passage and the inlet of the injection flow passage are not shared.

In this case, the one-way valve means 300 may be embedded or externally provided as illustrated in the figure.

Even in this case, a branch tube may be formed integrally with each of the cap hub 120 and the cylinder 20 and the branch tubes of them may be then connected by a tube made of a flexible material to each other. In addition, the branch tubes may be configured to be at certain angles and may also have a well-known configuration enabling selective connection or disconnection of the branch tubes.

In the configuration for disconnecting the branch tubes from each other, there would no leakage of the liquid medicine only if a state where the one-way valve means 300 is connected to the cylinder 20 should be maintained.

The one-way valve means 300 may be comprised of a soft sealing material and a pointed penetration needle configured to penetrate and be inserted into or to be detachable from the soft sealing material.

For example, if the cylinder 20 is provided with the sealing material such as silicone and the pointed penetration needle for penetrating the sealing material is also provided separately, in a state where the penetrating needle penetrates and is placed in the sealing material as in a vial, for example, the liquid medicine can be sucked into the cylinder 20. When the penetration needle is separated from the sealing material, an aperture in the sealing material generated by the penetration of the penetration needle is clogged to prevent the liquid medicine in the cylinder 20 from leaking through the sealing material.

(4) Fourth Embodiment

Example in which the inlet of the suction flow passage and the outlet of the injection flow passage are not coaxially arranged with each other, and the outlet of the suction flow passage and the inlet of the injection flow passage are not shared.

Finally, the fourth embodiment is a case in which, as shown in FIG. 18, the inlet of the suction flow passage and the outlet of the injection flow passage are not coaxially arranged with each other, and the outlet of the suction flow passage and the inlet of the injection flow passage are not shared.

Although FIG. 18 shows the example in which the one-way valve means 300 is embedded in the cap 100, the one-way valve means 300 may be formed in the flow passage extending from the cap 100 to the cylinder 20 or may be provided in the cylinder 20.

Again, as described above, the one-way valve means 300 may be implemented with the sealing material and the pointed penetration needle.

As a result, the liquid medicine sucked into the cap 100 is then sucked into the cylinder 20 through the one-way valve means 300, and the liquid medicine in the cylinder 20 can be injected into the body via the injection needle 10 after foreign substances contained in the liquid medicine are filtered out through the filter means 200 by removing the opening/closing means 400.

Therefore, the filtering syringe of the present invention has great advantages in that the inlet of the suction flow passage and the outlet of the injection flow passage are completely separated from each other so that foreign substances such as glass fragments may be fundamentally prevented from being injected together with the liquid medicine, and in that since the one-way valve means 300 may be externally provided, as required, there is no limitation on the size of the one-way valve means 300, whereby the suction of the liquid medicine can be smoothly performed with a smaller force.

Furthermore, by providing the filter means 200 on the injection flow passage, a large force is not required upon suction of the liquid medicine even through the filter means 200 having micro-pores is employed, and the liquid medicine is smoothly injected by a positive pressure upon injection of the liquid medicine.

The aforementioned embodiments are merely examples for specifically explaining the spirit of the present invention, and the scope of the present invention is not limited to the figures and embodiments.

| [Explanation of Reference Numerals] | |
|---|---|
| 10: Injection needle | 11: Needle body |
| 12: Hub | 13: Adhesive material |
| 20: Cylinder | 30: Plunger |
| 100: Cap | 110: Suction needle |
| 120: Cap hub | 121: Guide groove |
| 122: Engagement ledge | 200: Filter means |
| 300: One-way valve means | 310: Elastic plate |
| 311: Stepped portion | 321: Passage |
| 322: Opening | 330: Sphere |
| 331, 332: Valve seat | 350: Elastic band |
| 351: Flow hole | 352: Groove |
| 400: Opening/closing means | 410: Hermetic space |
| 420: Flange | 500: Connector |
| 600: Sealing means | |

The invention claimed is:

1. A filtering syringe comprising an injection needle, a cylinder and a plunger, the filtering syringe further comprising:

a suction flow passage formed from a pointed hollow cap to the cylinder and provided with a one-way valve, wherein the pointed hollow cap including a suction needle is coupled to the injection needle including a needle body while the needle body is inserted into the suction needle, such that the needle body of the injection needle is closed by a detachable opening/closing member upon suction of a liquid medicine; and an injection flow passage formed from the cylinder to the injection needle and provided with the detachable opening/closing member for selectively opening and closing the injection needle and a filter for filtering out foreign substances from the liquid medicine, wherein the detachable opening/closing member is separated from the injection needle to open the needle body upon injection of the liquid medicine, wherein the injection flow passage and the suction flow passage overlap partly each other or the injection flow passage is formed independently of the suction flow passage, whereby a flow passage portion from the filter to the injection needle in the injection flow passage is formed independently of the suction flow passage such that the liquid medicine is sucked in through the suction needle which is separated from the needle body of the injection needle, and is injected through the needle body of the injection needle.

2. The filtering syringe of claim 1, wherein an inlet of the suction flow passage and an outlet of the injection flow passage are coaxially arranged with each other, and an outlet of the suction flow passage and an inlet of the injection flow passage are shared.

3. The filtering syringe of claim 2, wherein an adhesive material for securing a needle body and a hub of the injection needle to each other is accommodated in the detachable opening/closing member so that the adhesive material is isolated from the liquid medicine, the detachable opening/closing member surrounding the injection needle to maintain airtightness.

4. The filtering syringe of claim 1, wherein an inlet of the suction flow passage and an outlet of the injection flow passage are not coaxially arranged with each other, and an outlet of the suction flow passage and an inlet of the injection flow passage are shared.

5. The filtering syringe of claim 4, wherein an adhesive material for securing a needle body and a hub of the injection needle to each other is accommodated in the detachable opening/closing member so that the adhesive material is isolated from the liquid medicine, the detachable opening/closing member surrounding the injection needle to maintain airtightness.

\* \* \* \* \*